United States Patent [19]

Struble

[11] Patent Number: 5,529,578
[45] Date of Patent: Jun. 25, 1996

[54] CARDIAC PACEMAKER WITH TRIGGERED MAGNET MODES

[75] Inventor: Chester Struble, Eijsden, Netherlands

[73] Assignee: Medtronic, Inc., Minneapolis, Minn.

[21] Appl. No.: 546,080

[22] Filed: Oct. 20, 1995

Related U.S. Application Data

[63] Continuation of Ser. No. 164,506, Dec. 9, 1993, abandoned.

[51] Int. Cl.$^6$ .................................................. A61N 1/37
[52] U.S. Cl. ............................................................ 607/29
[58] Field of Search ............................... 607/9, 14, 15, 607/17, 19, 29, 30, 27

[56] References Cited

U.S. PATENT DOCUMENTS

| | | |
|---|---|---|
| 3,311,111 | 3/1967 | Bowers . |
| 3,518,997 | 7/1970 | Sessions . |
| 3,623,486 | 11/1971 | Berkovits . |
| 3,631,860 | 1/1972 | Lopin . |
| 3,738,369 | 6/1973 | Adams et al. . |
| 3,805,796 | 4/1974 | Terry, Jr. et al. . |
| 4,066,086 | 1/1978 | Alferness et al. . |
| 4,208,008 | 6/1980 | Smith . |
| 4,211,235 | 7/1980 | Keller, Jr. et al. . |
| 4,233,985 | 11/1980 | Hartlaub et al. . |
| 4,236,524 | 12/1980 | Powell et al. . |
| 4,250,884 | 2/1981 | Hartlaub et al. . |
| 4,253,466 | 3/1981 | Hartlaub et al. . |
| 4,273,132 | 6/1981 | Hartlaub et al. . |
| 4,273,133 | 6/1981 | Hartlaub et al. . |
| 4,374,382 | 2/1983 | Markowitz . |
| 4,416,282 | 11/1983 | Saulson et al. ............................ 607/9 |
| 4,418,695 | 12/1983 | Buffet ........................................ 607/9 |
| 4,476,868 | 11/1984 | Thompson . |
| 4,539,992 | 9/1985 | Calfee et al. . |
| 4,550,732 | 11/1985 | Batty, Jr. et al. . |
| 4,556,063 | 12/1985 | Thompson et al. . |
| 4,571,589 | 2/1986 | Slocum et al. . |
| 4,676,248 | 6/1987 | Berntson . |
| 5,052,388 | 10/1991 | Sivula et al. . |
| 5,127,404 | 7/1992 | Wyborny et al. . |
| 5,243,979 | 9/1993 | Stein et al. ............................. 607/20 |
| 5,271,395 | 12/1993 | Wahlstrand et al. ..................... 607/9 |

FOREIGN PATENT DOCUMENTS

| | | | |
|---|---|---|---|
| 0058603 | 8/1982 | European Pat. Off. ................. | 607/29 |
| 1210850 | 2/1986 | U.S.S.R. ................................. | 607/29 |

OTHER PUBLICATIONS

Barold, S., Ed., "Modern Cardiac Pacing", Futura Publishing Company pp. 522–543. 1985.

Karbenn, et al., "Pacemaker–Induced Ventricular Tachycardia in Normally Functioning Ventricular Demand Pacemakers" American Journal Of Cardiology, Jan. 1, 1989 pp. 120–122.

Furman and Escher, Eds., "Modern Cardiac Pacing, A Clinical Overview", Charles Press, pp. 245–260. 1975.

Primary Examiner—William E. Kamm
Assistant Examiner—Jeffrey R. Jastrzab
Attorney, Agent, or Firm—Michael J. Jaro; Harold R. Patton

[57] ABSTRACT

An implantable pulse generator responsive to closure of a remotely actuable switch to operate in one or more triggered magnet modes, wherein intrinsic cardiac activity is continuously sensed. The pulse generator includes a timing mechanism for defining a predetermined triggered magnet mode interval. During triggered magnet mode operation, the pulse generator delivers pacing pulses at the end of each triggered magnet mode interval, provided that no intrinsic cardiac activity is sensed during the interval. Each time a stimulating pulse is delivered, the timing mechanism is reset and restarted to initiate another triggered magnet mode interval. The pulse generator is responsive to the sensing of intrinsic cardiac activity prior to expiration of a triggered magnet mode interval to deliver a non-competitive triggered stimulating pulse and to reset and restart the timing mechanism. In this way, competitive pacing and pacing during the vulnerable phase of a cardiac cycle is avoided. Upon discontinuance of switch closure, the pulse generator resumes operation in its previously programmed mode. Operation of the pulse generator in the triggered magnet mode does not interfere with other functions, such as threshold margin testing, battery depletion measurement, pace and sense threshold measurement, device interrogation and programming, and the like, normally associated with and performed during conventional magnet mode operation.

12 Claims, 3 Drawing Sheets

CARDIAC PACEMAKER WITH TRIGGERED MAGNET MODES

This application is a continuation of application Ser. No. 08/164,506 filed on Dec. 9, 1993, now abandoned.

FIELD OF THE INVENTION

This invention relates to the field of cardiac pacemakers, and more particularly relates to cardiac pacemakers operable in different pacing modes.

BACKGROUND OF THE INVENTION

Since the introduction of the first implantable pacemakers in the 1960's, there have been considerable advancements both in the field of electronics and the field of medicine, such that there is presently a wide assortment of commercially-available implantable medical devices. The class of implantable medical devices now includes not only pacemakers, but also implantable cardioverters, defibrillators, neural stimulators, and drug administering devices. Today's state-of-the-art implantable medical devices are vastly more sophisticated and complex than early pacemakers, capable of performing significantly more complex tasks. The therapeutic benefits of such devices have been well-proven.

As the functional sophistication and complexity of implantable medical devices has increased over the years, it has become increasingly more important for such devices to be equipped with a telemetry system for enabling them to communicate with an external unit.

For example, shortly after the introduction of the earliest fixed-rate, non-inhibited pacemakers, it became apparent that it would be desirable for a physician to non-invasively exercise at least some amount of control over the device, e.g., to turn the device on or off or adjust the fixed pacing rate, after implant. In early devices, one way the physician was able to have some control over implantable device operation was through the provision of a remotely and non-invasively actuable switch, such as a magnetic reed switch, in the implantable device. After implant, the reed switch would be actuated by placing a magnet over the implant site. Reed switch closure could then be used, for example, to alternately activate or deactivate the device. Alternatively, the fixed pacing rate of the device could be adjusted up or down by incremental amounts based upon the duration of reed switch closure. Many different schemes utilizing a reed switch to adjust parameters of implanted medical devices have been developed. See, for example, U.S. Pat. No. 3,311,111 to Bowers (one or more reed switches used to switch in and out resistors to control either the charging or discharging of an RC circuit to control the pulse rate); U.S. Pat. No. 3,518,997 to Sessions; U.S. Pat. No. 3,623,486 to Berkovits; U.S. Pat. No. 3,631,860 to Lopin (reed switch toggled to increment a counter for selecting from among four possible pacing rates); U.S. Pat. No. 3,738,369 to Adams et al.; U.S. Pat. No. 3,805,796 to Terry, Jr. (reed switch is repeatedly toggled to alter pulse repetition rate and output current of implanted pulse generator); and U.S. Pat. No. 4,066,086 to Alferness et al. (reed switch used to actuate a circuit for receiving radio-frequency signals).

As new, more advanced features are incorporated into implantable devices, it is typically necessary to convey correspondingly more information to the device relating to the selection and control of those features. For example, if a pacemaker is selectively operable in various pacing modes (identified using the well-known NASPE/BPEG pacemaker codes such as VVI, VDD, DDD, etc...), it is desirable that the physician or clinician be able to non-invasively select a mode of operation. Similarly, if the pacemaker is capable of pacing at various rates, or of delivering stimulating pulses of varying energy levels, it is desirable that the physician or clinician be able to select, on a patient-by-patient basis, appropriate values for such variable operational parameters.

Even greater demands are placed upon the telemetry system in implantable devices having such advanced features as rate adaptation based upon activity sensing, as disclosed, for example, in U.S. Pat. No. 5,052,388 to Sivula et al. entitled "Method and Apparatus for Implementing Activity Sensing in a Pulse Generator. The Sivula et al. '388 patent, which describes an implantable device commercially embodied as the Medtronic Legend™ pulse generator, is hereby incorporated by reference herein in its entirety.

The information which may need to be communicated to the implantable device in today's state-of-the-art pacemakers includes: pacing mode, multiple rate response settings, electrode polarity, maximum and minimum pacing rates, output energy (output pulse width and/or output current), sense amplifier sensitivity, refractory periods, calibration information, rate response attack (acceleration) and decay (deceleration), onset detection criteria, and perhaps many other parameter settings.

The need to be able to communicate more and more information to implanted devices quickly rendered the simple reed-switch closure arrangement insufficient. Also, it has become apparent that it would also be desirable not only to allow information to be communicated to the implanted device, but also to enable the implanted device to communicate information to the outside world.

For diagnostic purposes, for example, it is desirable for the implanted device to be able to communicate information regarding its operational status to the physician or clinician. State of the art implantable devices are available which can even transmit a digitized ECG signal for display, storage, and/or analysis by an external device.

Various telemetry systems for providing the necessary communications channels between an external unit and an implanted device have been shown in the art. Telemetry systems are disclosed, for example, in the following U.S. Patents: U.S. Pat. No. 4,539,992 to Calfee et al. entitled "Method and Apparatus for Communicating With Implanted Body Function Stimulator"; U.S. Pat. No. 4,550,732 to Batty Jr. et al. entitled "System and Process for Enabling a Predefined Function Within An Implanted Device"; U.S. Pat. No. 4,571,589 to Slocum et al. entitled "Biomedical Implant With High Speed, Low Power Two-Way Telemetry"; U.S. Pat. No. 4,676,248 to Berntson entitled "Circuit for Controlling a Receiver in an Implanted Device"; U.S. Pat. No. 5,127,404 to Wyborny et al. entitled "Telemetry Format for Implanted Medical Device"; U.S. Pat. No. 4,211,235 to Keller, Jr. et al. entitled "Programmer for Implanted Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above-referenced patents are employed in conjunction with an external programming/processing unit. One programmer for non-invasively programming a cardiac pacemaker is described in its various aspects in the following U.S. Patents to Hartlaub et al., each commonly assigned to the assignee of the present invention and each incorporated by reference herein in its entirety: U.S. Pat. No. 4,250,884 entitled "Apparatus For and Method Of Programming the Minimum Energy Threshold for Pacing Pulses to be Applied to a Patient's Heart"; U.S. Pat. No. 4,273,132 entitled "Digital Cardiac Pacemaker with Threshold Margin Check"; U.S. Pat. No. 4,273,133 entitled Programmable Digital Cardiac Pacemaker with Means to Override Effects of Reed Switch Closure"; U.S. Pat. No. 4,233,985 entitled "Multi-Mode Programmable Digital Cardiac Pacemaker"; and U.S. Pat. No. 4,253,466 entitled "Temporary and Permanent Programmable Digital Cardiac Pacemaker."

Aspects of the programmer that is the subject of the foregoing Hartlaub et al. patents (hereinafter "the Hartlaub programmer") are also described in U.S. Pat. No. 4,208,008 to Smith, entitled "Pacing Generator Programming Apparatus Including Error Detection Means" and in U.S. Pat. No. 4,236,524 to Powell et al., entitled "Program Testing Apparatus". The Smith '008 and Powell et al. '524 patents are also incorporated by reference herein in their entirety.

While the use of magnetic reed-switch closure alone for the communication of information to an implanted device has proven inadequate for programming all of the many programmable features of current state-of-the-art devices, many modem devices continue to incorporate a magnetic reed switch or other type of remotely-actuable switch in association with their telemetry systems. Often, as in the case of the Medtronic Activitrax™ and Spectrax™ pulse generators, for example, reed switch closure is required before radio-frequency programming signals from an external programmer will be accepted by the pulse generator. Such an arrangement provides a safeguard against accidental reprogramming of the pulse generator by spurious radio-frequency signals to which a pacemaker patient may be exposed.

In addition, pacemakers often enter a so-called "magnet mode" in response to reed switch closure. In conventional magnet mode, the pulse generator switches to an asynchronous fixed-rate pacing mode, where this fixed magnet mode pacing rate reflects the depletion level of the pulse generator's internal power supply (battery). Such operation is useful for a number of reasons. First, with the advanced programmable pacing and sensing features available with modem pulse generators, it can often be quite difficult for a physician or clinician to readily verify proper operation of the implanted device by simply looking at a surface EKG monitor. That is, it is often difficult to ascertain what events are being sensed by the device, how the device is responding to sensed events, and how the patient's heart is responding to the stimulating pulses generated by the pulse generator. When the pulse generator is pacing at its fixed, asynchronous magnet mode rate, however, it is much easier for the physician or clinician to determine, for example, whether the stimulating pulses have sufficient energy to exceed to patient's stimulation threshold.

Many pacemakers, for example the Medtronic Activitrax II, are further designed to modulate their magnet mode pacing rate according to the level of battery depletion. That is, the magnet mode pacing rate is reduced in proportion to the level of battery depletion. Thus, the physician can be made aware of the battery depletion and make an estimate of expected device longevity merely by affecting reed switch closure and observing the magnet mode pacing rate.

The Activitrax II also performs a "threshold margin test" upon initiation of its magnet mode of operation. In the threshold margin test, the pulse generator issues three stimulating pulses at an accelerated, asynchronous rate. The third of these three pulses has a reduced energy level relative to the programmed output energy level. The physician can observe on a surface EKG whether this reduced-energy third pulse has sufficient energy to capture the heart, in order to verify that the programmed output energy level includes an adequate stimulating threshold safety margin. After completion of the threshold margin test, the Activitrax II resumes asynchronous magnet mode pacing at a rate which reflects the level of battery depletion.

A pacemaker operable to perform a threshold margin test and then in an asynchronous magnet mode in response to reed switch closure as discussed above is described in greater detail in the above-referenced U.S. Pat. No. 4,273,132 to Hartlaub et al.

As those of ordinary skill in the art will appreciate, life-threatening heart rhythm disorders such as ventricular tachycardia (VT) or ventricular fibrillation (VF) can easily be activated with stimuli applied to cardiac tissue during the critical relative refractory period (T-wave)—"the vulnerable phase"—of each cardiac cycle. See, e.g., *Modem Cardiac Pacing*, Barold, ed., NY: Futura Publishing Co., (1985), pp. 522–543. See also, Leonard S. Dreifus, M.D., "Interrelationship of Ventricular Fibrillation and Cardiac Pacing" in *Modem Cardiac Pacing: A Clinical Overview*, Furman et al., eds., MD: Charles Press, (1975), pp. 245–260.

A pacing stimulus delivered during the atrial relative refractory period can also cause serious heart rhythm disorders, in particular, atrial flutter or even atrial fibrillation, in cases where atrial or dual-chamber pacemakers are used.

In view of the complications which may arise as a result of pacing the heart during its vulnerable phase, the inventor believes that it may be advantageous to provide for a variation of the conventional magnet mode of operation, wherein pacing in the vulnerable phase of the cardiac cycle is avoided.

SUMMARY OF THE INVENTION

In accordance with one aspect of the present invention, therefore, there is provided an implantable pulse generator responsive to application of a magnet causing reed switch closure to operate in an alternate magnet mode wherein the pulse generator is prevented from delivering pacing pulses during the T-wave portion of the patient's cardiac cycle.

In accordance with another aspect of the present invention, competitive pacing, wherein delivery of stimulating pulses interferes with spontaneous cardiac rhythm, is avoided.

In accordance with still another aspect of the present invention, a pulse generator is provided wherein the conventional functions performed during magnet mode operation, such as modulation of pacing rate according to battery depletion, device interrogation, threshold margin testing, auto-threshold testing and the like may still be performed with the pulse generator operating in the alternate magnet mode.

The foregoing and other aspects of the present invention are embodied in a programmable implantable pulse generator operable in one or more alternate magnet modes wherein intrinsic electrical cardiac activity is continuously sensed, and wherein intrinsic electrical cardiac activity triggers delivery by the pulse generator of a stimulating pulse.

A timing mechanism within the pulse generator initiates a triggered magnet mode pacing interval upon delivery of each stimulating pulse during magnet mode. If no intrinsic activity is detected during the triggered magnet mode pacing interval, a stimulating pulse is delivered upon expiration of the interval, and the timing mechanism is reset and restarted. If intrinsic activity is detected during the triggered magnet mode pacing interval, a non-competitive triggered stimulating pulse is immediately delivered. Upon delivery of such a triggered stimulating pulse, the timing mechanism is again reset and restarted, such that a new triggered magnet mode pacing interval is initiated.

BRIEF DESCRIPTION OF THE DRAWINGS

The foregoing and other features of the present invention will be best appreciated with reference to the following detailed description of a specific embodiment of the invention, when read in conjunction with the accompanying drawings, wherein.

DETAILED DESCRIPTION OF A SPECIFIC EMBODIMENT OF THE INVENTION

Figure 1:
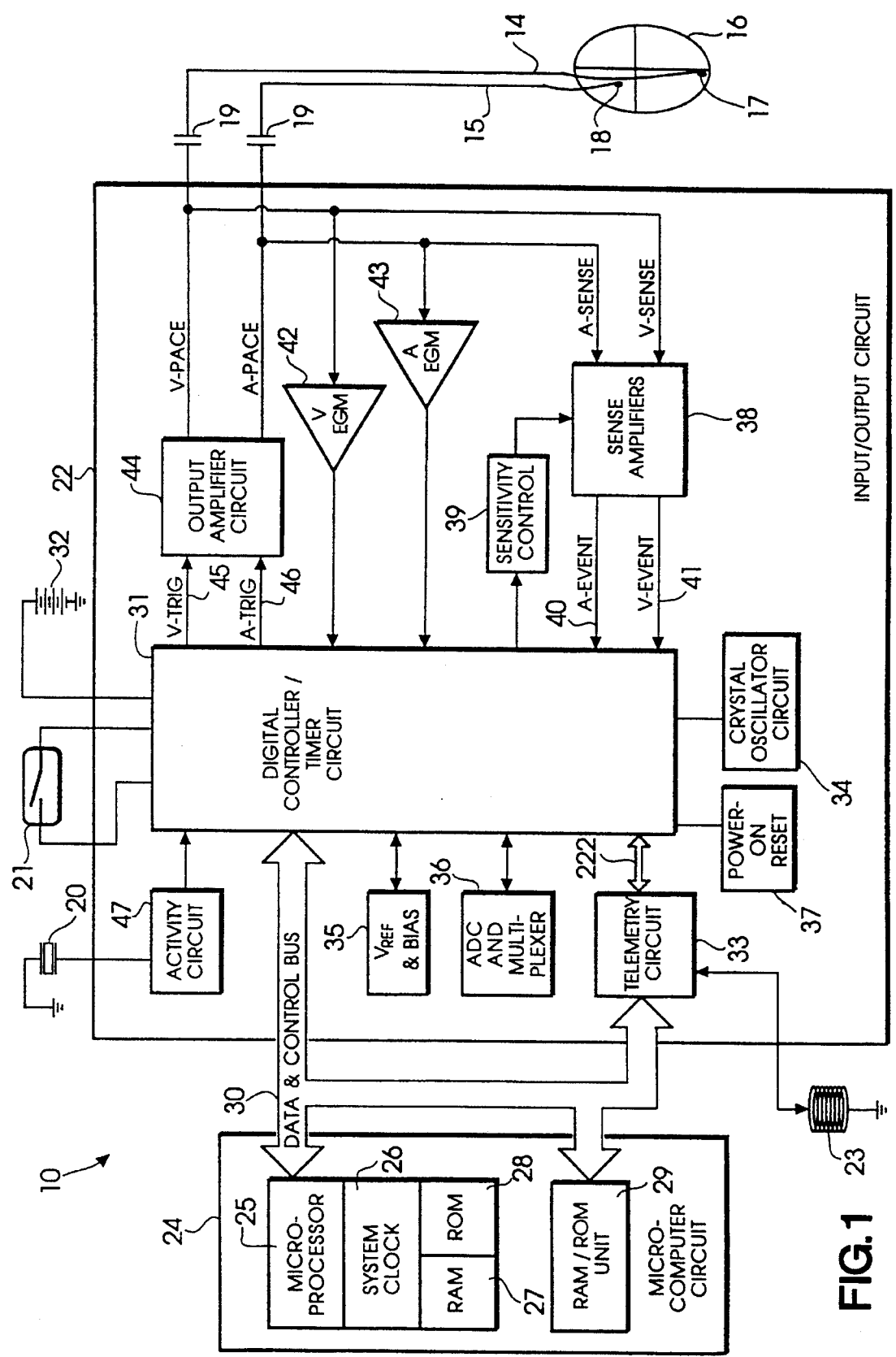
FIG. 1 is a block diagram of a cardiac pacemaker in accordance with one embodiment of the invention.

Referring to FIG. 1, there is shown a block diagram of an implantable pulse generator 10 which is operable in accordance with the principles of the present invention. Although the present invention will be described herein in conjunction with a pulse generator 10 having a microprocessor-based architecture, it will be understood that pulse generator 10 may be implemented in any logic based, custom integrated circuit architecture, if desired. The pulse generator 10 shown in FIG. 1 is substantially similar to that disclosed in U.S. Pat. No. 5,243,979 of Paul Stein and entitled "Method and Apparatus for Implementing Activity Sensing in a Pulse Generator", and in the pending U.S. patent application Ser. No. 07/870,062 filed Apr. 17, 1992 by Wahlstrand et al. entitled "Method and Apparatus for Rate-Responsive Cardiac Pacing" now U.S. Pat. No. 5,271,395 each of which is incorporated herein by reference in their entirety.

Although a particular implementation of a pulse generator is disclosed herein, it is to be understood that the present invention may be advantageously practiced in conjunction with many different types of pulse generators, such as that described in the above-referenced Sivula et al. patent, for example, as well as other types of implantable medical devices. It is to be understood, for example, that although an activity-sensing rate-responsive pulse generator is described herein, the present invention is by no means limited in its application to this type of device. It is contemplated that the present invention may be advantageously incorporated into a wide variety of implantable pulse generators, including both single- and dual-chamber pacemakers.

In FIG. 1, pulse generator 10 is shown to include an activity sensor 20, which may be, for example, a piezoelectric element bonded to the inside of the pacemaker's shield. Such a pacemaker/activity sensor configuration is the subject of the above-referenced patent to Anderson et al. Piezoelectric sensor 20 provides a sensor output which varies as a function of a measured parameter that relates to the metabolic requirements of a patient.

Pulse generator 10 of FIG. 1 is programmable by means of an external programming unit (not shown). One such programmer suitable for the purposes of the present invention is the Medtronic Model 9760 programmer which is commercially available and is intended to be used with all Medtronic pulse generators. The 9760 programmer is a microprocessor-based device which provides a series of encoded signals to pulse generator 10 by means of a programming head which transmits radio-frequency (RF) encoded signals to pulse generator 10 according to the telemetry system laid out, for example, in U.S. Pat. No. 5,127,404 to Wyborny et al. entitled "Improved Telemetry Format", which is assigned to the assignee of the present invention and which is incorporated herein by reference in its entirety. It is to be understood, however, that the programming methodology disclosed in the above-referenced patent is identified herein for the purposes of illustration only, and that any programming methodology may be employed so long as the desired information can be conveyed between the pulse generator and the external programmer.

It is believed that one of skill in the art would be able to choose from any of a number of available pacemaker programmers and programming techniques to accomplish the tasks necessary for practicing the present invention. As noted above, however, the Medtronic Model 9760 programmer is presently preferred by the inventors.

In the illustrative embodiment of the present invention, parameters such as the lower rate of pulse generator 10 may be programmable, for example from 40 to 90 pulses per minute (PPM) in increments of 10 PPM, and the upper rate may be programmable, for example, between 100 and 175 PPM in 25 PPM increments. There may also be programmable rate response functions in pulse generator 10.

With continued reference to FIG. 1, pulse generator 10 is further provided with a reed switch 21, remotely actuable by means of a magnet (not shown) brought into proximity of pulse generator 10, in accordance with common practice in the art. As shown in FIG. 1, reed switch 21 is coupled to digital controller/timer circuit 31, such that reed switch closure can be used as a means of non-invasively communicating with pulse generator 10. In particular, and also in accordance with common practice in the art, reed switch closure must occur in conjunction with the initiation of any programming session for pulse generator 10. Also, pulse generator 10 in accordance with the presently disclosed embodiment of the invention is responsive to reed switch closure to begin operating in a particular magnet mode of operation, as will be hereinafter described in greater detail.

Pulse generator 10 is schematically shown in FIG. 1 to be electrically coupled via pacing lead 14 and 15 to a patient's heart 16. Leads 14 and 15 include one or more intracardiac electrodes, designated as 17 and 18 in FIG. 1, located near the distal ends of leads 14 and 15, respectively, and positioned within the right ventricular (RV) and right atrial (RA) chambers, respectively, of heart 16. Leads 14 and 15 can be of either the unipolar or bipolar type as is well known in the art; alternatively, a single, multiple-electrode lead may be used.

Electrodes 17 and 18 are coupled via suitable lead conductors through input capacitors 19 to input/output terminals of an input/output circuit 22. In the presently disclosed embodiment, activity sensor 20 is bonded to the inside of the pacemaker's outer protective shield, in accordance with common practice in the art. As shown in FIG. 1, the output from activity sensor 20 is also coupled to input/output circuit 22.

Input/output circuit 22 contains the analog circuits for interface to the heart 16, activity sensor 20, an antenna 23, as well as circuits for the application of stimulating pulses to heart 16 to control its rate as a function thereof under control of the software-implemented algorithms in a microcomputer circuit 24.

Microcomputer circuit 24 comprises a microprocessor 25 having an internal system clock circuit 26, and on-board RAM 27 and ROM 28. Microcomputer circuit 24 further comprises a RAM/ROM unit 29. Microprocessor 25 and RAM/ROM unit 29 are each coupled by a data and control bus 30 to a digital controller/timer circuit 31 within input/output circuit 22. Microcomputer circuit 24 may be a commercially-available, general-purpose microprocessor or microcontroller, or may be a custom integrated circuit device augmented by standard RAM/ROM components.

It will be understood that each of the electrical components represented in FIG. 1 is powered by an appropriate implantable battery power source 32, in accordance with common practice in the art. For the sake of clarity, the coupling of battery power to the various components of pulse generator 10 has not been shown in the FIGS.

An antenna 23 is connected to input/output circuit 22 for purposes of uplink/downlink telemetry through an RF telemetry circuit 33 in accordance with one embodiment of the invention, to be hereinafter described in greater detail. In the embodiment of FIG. 1, telemetry circuit 33 is coupled to digital controller/timer circuit 31. It is contemplated that telemetry circuit 33 may also be coupled directly to microcomputer circuit 24 via data and control bus 30.

A crystal oscillator circuit 34, typically a 32,768-Hz crystal-controlled oscillator, provides main timing clock signals to digital controller/timer circuit 31. A $V_{REF}$ and Bias circuit 35 generates stable voltage reference and bias currents for the analog circuits of input/output circuit 22. An analog-to-digital converter (ADC) and multiplexer unit 36 digitizes analog signals and voltages to provide "real-time" telemetry intracardiac signals and battery end-of-life (EOL) replacement function. A power-on-reset (POR) circuit 37 functions as a means to reset circuitry and related functions to a default condition upon detection of a low battery condition, which will occur upon initial device power-up or will transiently occur in the presence of electromagnetic interference, for example.

The operating commands for controlling the timing of pulse generator 10 are coupled by bus 30 to digital controller/timer circuit 31 wherein digital timers and counters are employed to establish the overall escape interval of the pacemaker, as well as various refractory, blanking, and other timing windows for controlling the operation of the peripheral components within input/output circuit 22.

Digital controller/timer circuit 31 is coupled to sensing circuitry including a sense amplifier circuit 38 and a sensitivity control circuit 39. In particular, digital controller/timer circuit 31 receives an A-EVENT (atrial event) signal on line 40, and a V-EVENT (ventricular event) signal on line 41. Sense amplifier circuit 38 is coupled to leads 14 and 15, in order to receive the V-SENSE (ventricular sense) and A-SENSE (atrial sense) signals from heart 16. Sense amplifier circuit 38 asserts the A-EVENT signal on line 40 when an atrial event (i.e., a paced or intrinsic atrial event) is detected, and asserts the V-EVENT signal on line 41 when a ventricular event (paced or intrinsic) is detected. Sense amplifier circuit 38 includes one or more sense amplifiers corresponding, for example, to that disclosed in U.S. Pat. No. 4,379,459 issued to Stein on Apr. 12, 1983, incorporated by reference herein in its entirety.

Sensitivity control 39 is provided to adjust the gain of sense amplifier circuitry 38 in accordance with programmed sensitivity settings, as would be appreciated by those of ordinary skill in the pacing art.

A V-EGM (ventricular electrocardiogram) amplifier 42 is coupled to lead 14 to receive the V-SENSE signal from heart 16. Similarly, an A-EGM (atrial electrocardiogram) amplifier 43 is coupled to lead 15 to receive the A-SENSE signal from heart 16. The electrogram signals developed by V-EGM amplifier 42 and A-EGM amplifier 43 are used on those occasions when the implanted device is being interrogated by an external programmer (not shown), to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference in its entirety.

Digital controller and timer circuit 31 is coupled to an output amplifier circuit 44 via two lines 45 and 46, designated V-TRIG (ventricular trigger) and A-TRIG (atrial trigger), respectively. Circuit 31 asserts the V-TRIG signal on line 45 in order to initiate the delivery of a ventricular stimulating pulse to heart 16 via pace/sense lead 14. Likewise, circuit 31 asserts the A-TRIG signal on line 46 to initiate delivery of an atrial stimulating pulse to heart 16 via pace/sense lead 15. Output amplifier circuit 44 provides a ventricular pacing pulse (V-PACE) to the right ventricle of heart 16 in response to the V-TRIG signal developed by digital controller/timer circuit 31 each time the ventricular escape interval times out, or an externally transmitted pacing command has been received, or in response to other stored commands as is well known in the pacing art. Similarly, output amplifier circuit 44 provides an atrial pacing pulse (A-PACE) to the right atrium of heart 16 in response to the A-TRIG signal developed by digital controller/timer circuit 31. Output amplifier circuit 44 includes one or more output amplifiers which may correspond generally to that disclosed in U.S. Pat. No. 4,476,868 issued to Thompson on Oct. 16, 1984 also incorporated herein by reference in its entirety.

As would be appreciated by those of ordinary skill in the art, input/output circuitry will include decoupling circuitry for temporarily decoupling sense amplifier circuit 38, V-EGM amplifier 45 and A-EGM amplifier 46 from leads 14 and 15 when stimulating pulses are being delivered by output amplifier circuit 44. For the sake of clarity, such decoupling circuitry is not depicted in FIG. 2.

While specific embodiments of sense amplifier circuitry, output amplifier circuitry, and EGM amplifier circuitry have been identified herein, this is done for the purposes of illustration only. It is believed by the inventor that the specific embodiments of such circuits are not critical to the present invention so long as they provide means for generating a stimulating pulse and provide digital controller/timer circuit 31 with signals indicative of natural and/or stimulated contractions of the heart. It is also believed that those of ordinary skill in the art could chose from among the various well-known implementations of such circuits in practicing the present invention.

Digital controller/timer circuit 31 is coupled to an activity circuit 47 for receiving, processing, and amplifying activity signals received from activity sensor 20. A suitable implementation of activity circuit 47 is described in detail in the above-referenced Sivula et al. application. It is believed that the particular implementation of activity circuit 47 is not critical to an understanding of the present invention, and that various activity circuits are well-known to those of ordinary skill in the pacing art. Moreover, and as previously noted, it is not believed that the present invention is limited in its application only to devices capable of activity sensing.

As a dual-chamber device, pulse generator 10 in accordance with the presently disclosed embodiment of the invention is controlled by microcomputer circuit 24 and digital controller/timer circuit 31 to operate in any one of several pacing modes, including DDD, DDI, DVI, VDD, VVI, VVT, VOO, AAI, AAT, and AOO. The operating mode of pulse generator 10 is programmable in the conventional manner using an external programmer, as previously described. Those of ordinary skill in the art will be familiar with the operation of pulse generator 10 in such modes, and the particulars relating to such operation will not be described herein in detail.

Those of ordinary skill in the art will also appreciate that in conventional pulse generators of the prior art, placing a magnet over the implant site of the device causes reed switch closure, thereby causing the device to enter one of several magnet modes of operation. If the pulse generator was previously programmed to a single-chamber ventricular pacing mode, e.g., VVI, reed switch closure would cause the device to begin operating in an asynchronous, fixed rate magnet mode VOO. Similarly, if the device was previously programmed to a single-chamber atrial mode, e.g., AAI, reed switch closure would cause the device to begin operating in an atrial magnet mode AOO. If the device was previously programmed to a dual-chamber pacing mode, e.g., DDD, reed switch closure would cause the device to operate in a dual-chamber magnet mode DOO.

Figure 2:
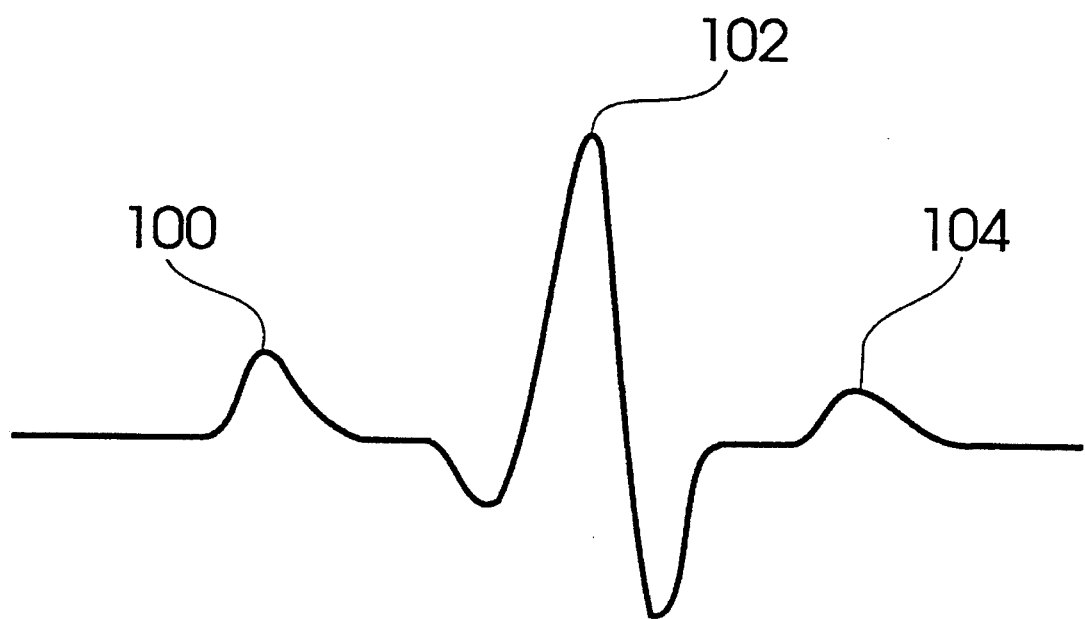
FIG. 2 illustrates an electrical waveform corresponding to a human cardiac cycle.

When pacing in one of the fixed rate, asynchronous magnet modes VOO, AOO, or DOO, there is some risk that a pulse generator will deliver a pacing stimulus during the vulnerable phase of a cardiac cycle, i.e., during the ventricular repolarization phase or T-wave. Those of ordinary skill in the art will recognize that, as depicted in FIG. 2, the human cardiac cycle is represented electrically as a complex wave consisting of several phases. In FIG. 2, the first phase, called a P-wave, is designated with reference numeral 100. The P-wave electrically represents an atrial beat associated with atrial depolarization.

The major and most pronounced electrical pulse in the cardiac cycle is the R-wave, designated as 102 in FIG. 2, which stimulates and represents ventricular contraction. R-waves are normally generated by depolarization of the ventricles, but when not so produced due to some cardiac malfunction, it is the function of an artificial pacemaker to provide periodic electrical pulses to the heart to supply a missing R-wave.

A T-wave portion 104 of the cardiac cycle of FIG. 2 follows R-wave 102. Within the T-wave is the critical interval known as the "vulnerable phase" of the cardiac cycle. In some cases, a pacemaker stimulating pulse delivered to the heart during this period can conceivably elicit bursts of ventricular tachycardia or fibrillation which are, of course, undesirable.

In accordance with one aspect of the present invention, therefore, pulse generator 10 of FIG. 1 is responsive to closure of reed switch 21 to operate in one or more alternative magnet modes of operation, hereinafter referred to as "triggered magnet modes" and designated with the codes $AAT_M$ (atrial triggered magnet mode), $VVT_M$ (ventricular triggered magnet mode), and $DDT_M$ (dual-chamber triggered magnet mode). In these triggered magnet modes, sensing of cardiac electrical signals is continuously carded on, such that delivery of stimulating pulses during the vulnerable phase of a cardiac cycle can be avoided. Those of ordinary skill in the art will appreciate that such operation represents a departure from prior art magnet modes, which are most often fixed-rate and asynchronous (i.e., no sensing is performed).

Figure 3:
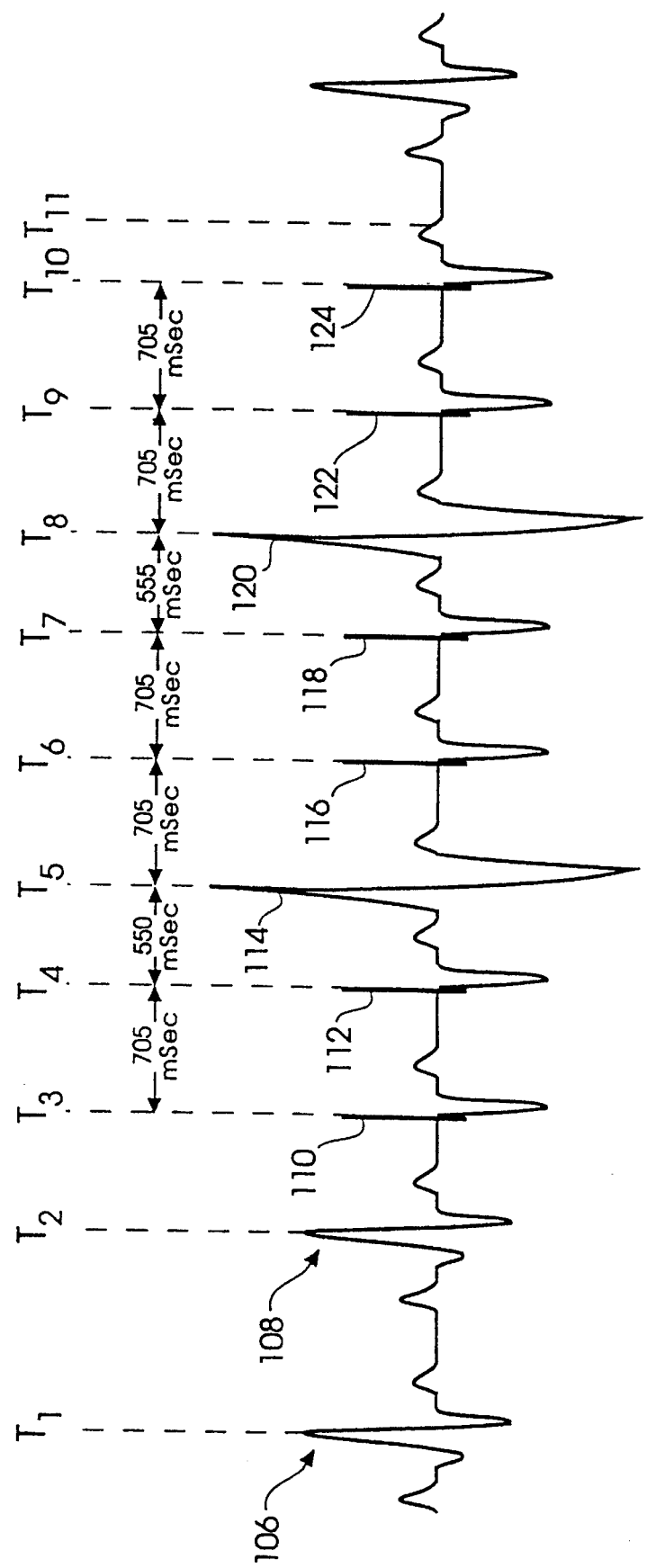
FIG. 3 illustrates an electrical waveform corresponding to a sequence of cardiac cycles during operation of the pacemaker of FIG. 1.

The presently disclosed embodiment of the invention may perhaps be best appreciated with reference to FIG. 3, in which there is shown a voltage waveform representing a sequence of successive cardiac cycles. In FIG. 3, a first intrinsic R-wave 106 is sensed by sense amplifiers 38 in pulse generator 10 of FIG. 1. R-wave 106 is detected a time designated $T_1$ in FIG. 3. Similarly, approximately one second later at time $T_2$ in FIG. 3, a second intrinsic R-wave 108 is detected.

At time $T_3$ in FIG. 3, a magnet is applied over the implant site of pulse generator 10, such that closure of reed switch 21 therein occurs. Closure of reed switch 21 is detected by digital controller/timer circuit 31, which in turn begins to operate in a triggered magnet mode in accordance with the presently disclosed embodiment of the invention. In particular, it will be assumed for the purposes of the illustration of FIG. 3 that pulse generator 10 has been previously programmed into a single-chamber ventricular pacing mode, such as VVI, so that upon application of a magnet to effect closure of reed switch 21 at time $T_3$, pulse generator 10 enters the ventricular triggered magnet mode $VVT_M$ in accordance with the presently disclosed embodiment of the invention.

Upon entering the $VVT_M$ mode, digital controller/timer circuit 31 issues a V-TRIG signal on line 45 (see FIG. 1), causing output amplifier circuit 44 to produce a V-PACE stimulating pulse which is conveyed to the heart 16 via ventricular lead 14. The artifact of this pacing pulse is designated with reference numeral 110 in FIG. 3.

Also at time $T_3$ in FIG. 3, a timer within digital controller/timer circuit is activated to begin timing a magnet mode pacing interval. In the presently preferred embodiment of the invention, this magnet mode pacing interval will reflect an increase (e.g., 10%) over the programmed pacing rate for pulse generator 10, in accordance with conventional practice. Additionally, the magnet mode pacing interval may be modulated according to the level of battery depletion, also in accordance with common practice in the art.

In the embodiment of the invention represented by FIG. 3, a magnet mode pacing interval of 705-mSec is provided, this corresponding to a triggered magnet mode pacing rate of approximately 85 pulses per minute (PPM). Thus, upon expiration of the 705-mSec triggered magnet mode pacing interval at time $T_4$ in FIG. 3, another pacing stimulus 112 is delivered to the ventricle. Also at time $T_4$, the magnet mode pacing interval timer is reset and restarted to being timing another magnet mode pacing interval. However, as shown in FIG. 3 an intrinsic ventricular contraction is detected in sense amplifiers 38 at time $T_5$, only 550-mSec after time $T_4$. In accordance with the presently disclosed embodiment of the invention, this premature ventricular contraction at time $T_5$ triggers the delivery of a ventricular stimulating pulse at time $T_5$, prior to expiration of the 705-mSec magnet mode pacing interval.

Upon delivery of the triggered stimulating pulse at time $T_5$, the magnet mode interval timer is reset and restarted to begin timing a new 705-mSec interval. This interval expires at time $T_6$ prior to detection of any intrinsic activity. Thus, a ventricular pulse 116 is delivered, and the magnet mode timing interval restarted. Another magnet mode interval expires at time $T_7$, once again prior to detection of intrinsic cardiac activity. Thus, a stimulating pulse 118 is delivered at time $T_7$.

At time $T_8$, prior to expiration of the magnet mode timing interval initiated at time $T_7$, an intrinsic ventricular contraction 120 is detected, triggering the immediate delivery of a stimulating pulse at time $T_8$. Thereafter, two more 705-mSec magnet mode pacing intervals elapse without detection of intervening intrinsic activity, leading to delivery of stimulating pulses 122 and 124 at times $T_9$ and $T_{10}$, respectively, at the magnet mode rate. At time $T_{11}$, the magnet is removed from the implant site of pulse generator 10, so that closure of reed switch 21 is discontinued. In response to the opening of reed switch 21, digital controller/timer circuit 31 ceases operation in the triggered magnet mode and resumes operation in the previously programmed mode.

Those of ordinary skill in the art will appreciate that in the triggered magnet mode described above with reference to FIGS. 1 and 3, the delivery of stimulating pulses during the vulnerable phase of cardiac cycles is avoided through the continuous sensing of electrical cardiac signals during operation in magnet mode, and through the delivery of triggered pacing stimuli and resetting of the magnet mode pacing interval upon detection of intrinsic activity prior to the elapse of a magnet mode pacing interval.

In accordance with one aspect of the present invention, it is contemplated that the triggered magnet mode operation in accordance with the present invention will not interfere with the additional functions which are often associated with and performed during magnet mode operation in prior art devices, such as threshold margin testing, pacing and sensing threshold measurement, device interrogation, device programming, and battery depletion measurements, can be performed.

The foregoing description of a particular embodiment of the invention involved pulse generator 10 being initially programmed to a ventricular pacing mode. It is believed that it will be readily apparent to those of ordinary skill in the art having the benefit of this disclosure that the present invention may be equally advantageously practiced in the context of atrial and dual-chamber pacemakers. In cases with atrial pacemakers or dual-chamber pacemakers, the occurrence of triggered spikes (such as 114 and 120 in FIG. 3) will indicate the exact time at which intrinsic atrial signals have been sensed. It is believed that this is advantageous, as it will facilitate the discrimination between supraventricular and ventricular tachyarrhythmias.

From the foregoing detailed description of a specific embodiment of the invention, it should be apparent that a pulse generator operable in triggered magnet modes has been disclosed, wherein delivery of asynchronous stimulating pulses during the vulnerable phase of a cardiac cycle is avoided, thus reducing the risk of initiating an episode of ventricular tachycardia or ventricular fibrillation. Although a specific embodiment of the invention has been described herein in some detail, it is to be understood that this has been done for the purposes of illustration only, and is not intended to be limiting with respect to the scope of the invention. It is contemplated that various substitutions, alterations, and/or modifications, including but not limited to those specifically discussed herein, may be made to the disclosed embodiment without departing from the spirit and scope of the present invention as defined in the appended claims, which follow.

What is claimed is:

1. A pulse generator, implantable in a patient, comprising:

a means for providing power;

an output circuit, responsive to a triggering signal to generate an electrical stimulating pulse, said output circuit coupled to said means for providing power;

at least one conductive lead, coupled to said output circuit, said conductive lead to conduct said stimulating pulse from said output circuit to a patient's heart and to conduct an electrical signal generated by a cardiac event from said patient's heart to said pulse generator;

a sensing circuit, coupled to said conductive lead to sense an occurrence of a predetermined cardiac event and to issue a detection signal upon the sensing of said predetermined cardiac event;

a remotely actuable switch having an output terminal, said switch having means for asserting a mode control signal on said output terminal when said switch is actuated;

a control circuit, coupled to said output circuit, said sensing circuit, and to said remotely actuable switch output terminal, said control circuit having means for responding to assertion of said mode control signal to issue a series of said triggering signals wherein each two successive triggering signals in said series is separated in time by the lesser of: (a) a fixed pacing time interval; and (b) a time interval beginning with the first of said two successive triggering signals and ending with the issuance of said detection signal.

2. A pulse generator in accordance with claim 1, wherein said remotely-actuable switch is a magnetic reed switch.

3. A pulse generator in accordance with claim 1, said means for providing power comprises a battery coupled to said control circuit.

4. A pulse generator, implantable in a patient, comprising:

a means for providing power;

a ventricular output circuit, responsive to a ventricular triggering signal to generate a ventricular stimulating pulse, said ventricular output circuit coupled to said means for providing power;

an atrial output circuit, responsive to an atrial triggering signal to generate an atrial stimulating pulse, said atrial output circuit coupled to said means for providing power;

a ventricular conductor, coupled to said ventricular output circuit to conduct said ventricular stimulating pulse to a ventricle of said patient;

an atrial conductor, coupled to said atrial output circuit to conduct said atrial stimulating pulse to an atrium of said patient;

a sensing circuit, electrically coupled to said patient's heart to sense an occurrence of a predetermined cardiac event and to issue a detection signal upon the sensing of said predetermined cardiac event;

a remotely actuable switch having an output terminal, said switch having means for asserting a mode control signal on an output terminal thereof when said switch is in a first position;

a control circuit, coupled to said ventricular output circuit, said atrial output circuit, said sensing circuit, and to said remotely-actuable switch, said control circuit responsive to said mode control signal to issue an alternating series of said atrial and ventricular triggering signals wherein an atrial triggering signal is issued a first predetermined time interval after each ventricular triggering signal, and wherein for each atrial triggering signal, the time interval between said atrial triggering signal and a subsequent ventricular triggering signal is the lesser of: (a) a second predetermined time interval; and (b) a time interval beginning with said atrial triggering signal and ending with the issuance of said detection signal.

5. A pulse generator in accordance with claim 4, wherein said remotely-actuable switch is a magnetic reed switch.

6. A pulse generator in accordance with claim 4, wherein means for providing power comprises a battery coupled to said control circuit.

7. A method of operating an implantable pulse generator responding to manual actuation of a mode control switch comprising:

(a) manually actuating a mode control switch;

(b) initiating a predetermined, fixed timing interval and detecting a cardiac event which occurs within the time of said predetermined, fixed timing interval;

(c) issuing a stimulating pulse immediately in response to said detected cardiac event which occurs within the time of said predetermined, fixed timing interval;

(d) if no cardiac event is detected in step (c), issuing said stimulating pulse upon expiration of said fixed timing interval; and (e) repeating steps (b) through (d) so long as said mode control switch is actuated.

8. A method in accordance with claim 7, wherein said step of manually actuating a mode control switch comprises manually actuating a magnetically-actuated reed switch.

9. An implantable pulse generator comprising:

means for providing power;

means for generating an electrical stimulating pulse in response to a triggering signal, the means for generating coupled to the means for providing power;

means for electrically coupling the means for generating to a patient's heart, the means for generating coupled to the means for electrically coupling;

means for sensing an occurrence of a predetermined cardiac event, the means for sensing issuing a detection signal upon sensing of the predetermined cardiac event, the means for sensing coupled to the means for electrically coupling, the means for sensing coupled to the means for generating; and means for controlling the means for generating, the means for controlling switchable between a first mode and a second mode by a means for remotely switching, wherein in the first mode the means for controlling issues a series of triggering signals wherein each two successive triggering signals in the series is separated in time by the lesser of: (a) a fixed pacing time interval; and (b) a time interval beginning with the first of the two successive triggering signals and ending with the issuance of the detection signal.

10. An implantable pulse generator in accordance with claim 9, wherein the means for remotely switching comprises a magnetic reed switch.

11. An implantable pulse generator comprising:

a battery;

a generator emitting an electrical stimulating pulse in response to a triggering signal, the generator coupled to the battery;

a lead for coupling the generator to a patient's heart, the generator coupled to the lead;

a sensor for sensing a predetermined cardiac event, the sensor issuing a detection signal upon the sensing of the predetermined cardiac event, the sensor coupled to the lead; and a controller, the controller coupled to the generator, the controller coupled to the sensor, the controller switchable between a first mode and a second mode by a remotely switchable switch, wherein in the first mode the controller issues a series of triggering signals wherein each two successive triggering signals in the series are separated in time by the lesser of: (a) a fixed pacing time interval; and (b) a time interval beginning with the first of the two successive triggering signals and ending with the issuance of the detection signal.

12. An implantable pulse generator in accordance with claim 11, wherein the remotely switchable switch comprises a magnetic reed switch.

* * * * *